United States Patent [19]

Reich et al.

[11] Patent Number: 5,791,352
[45] Date of Patent: Aug. 11, 1998

[54] METHODS AND COMPOSITIONS FOR INHIBITING TISSUE ADHESION

[75] Inventors: Cary J. Reich, Los Gatos; Donald Wallace, Menlo Park; Greg Dapper, Newark, all of Calif.

[73] Assignee: Fusion Medical Technologies, Inc., Mountain View, Calif.

[21] Appl. No.: 758,267

[22] Filed: Nov. 8, 1996

Related U.S. Application Data

[63] Continuation-in-part of Ser. No. 673,710, Jun. 19, 1996.

[51] Int. Cl.$^6$ ................................. A61B 19/00
[52] U.S. Cl. .................. 128/898; 606/213; 606/214; 606/215; 602/904
[58] Field of Search ............... 128/898; 606/2–4, 606/7–17, 213–215; 623/11; 602/904; 424/484, 486, 488, 426–428; 514/772.1, 772.3, 728, 729

[56] References Cited

U.S. PATENT DOCUMENTS

| | | |
|---|---|---|
| 4,603,695 | 8/1986 | Ikada et al. |
| 4,674,488 | 6/1987 | Nashef et al. |
| 4,854,320 | 8/1989 | Dew et al. ............... 128/397 |
| 4,889,722 | 12/1989 | Sheffield et al. |
| 4,911,926 | 3/1990 | Henry et al. |
| 4,937,254 | 6/1990 | Sheffield et al. |
| 4,937,270 | 6/1990 | Hamilton et al. |
| 5,017,229 | 5/1991 | Burns et al. |
| 5,068,225 | 11/1991 | Pennell et al. |
| 5,071,417 | 12/1991 | Sinofsky. |
| 5,126,141 | 6/1992 | Henry. |

(List continued on next page.)

FOREIGN PATENT DOCUMENTS

| | | |
|---|---|---|
| 0 372 969 | 6/1990 | European Pat. Off. |
| 0 416 250 | 3/1991 | European Pat. Off. |
| 0 426 368 | 5/1991 | European Pat. Off. |
| 0 608 139 | 7/1991 | European Pat. Off. |
| 0 608 921 | 8/1994 | European Pat. Off. |
| 0 610 731 | 8/1994 | European Pat. Off. |
| 0 645 150 | 3/1995 | European Pat. Off. |
| 0 669 138 | 8/1995 | European Pat. Off. |
| WO 95/15343 | of 0000 | WIPO. |
| WO 93/13137 | 7/1992 | WIPO. |
| WO 92/20349 | 11/1992 | WIPO. |
| WO 92/21354 | 12/1992 | WIPO. |
| WO 92/22312 | 12/1992 | WIPO. |
| WO 93/16687 | 9/1993 | WIPO. |
| WO 93/17669 | 9/1993 | WIPO. |
| WO 94/02517 | 2/1994 | WIPO. |
| WO 94/08635 | 5/1994 | WIPO. |
| WO 94/21324 | 9/1994 | WIPO. |
| WO 94/24962 | 11/1994 | WIPO. |
| WO 95/09883 | 4/1995 | WIPO. |
| WO 95/15747 | 6/1995 | WIPO. |

OTHER PUBLICATIONS

Abstract, Abstract No. 111:45215, Miyata et al. Biodegradable Antiadhesive Membrane, Jinko Zoki (1989), 18(1), 93–6.

Oz et al. "Preliminary report: laser welding and fibrinogen soldering are superior to sutured cholecyctostomy closure in a canine model." SPIE 1200:55–59, 1990.

*Primary Examiner*—Vincent Millin
*Assistant Examiner*—Kelly O'Hara
*Attorney, Agent, or Firm*—Townsend and Townsend and Crew LLP

[57] ABSTRACT

Tissue adhesions are inhibited by applying and immobilizing a solid preformed matrix material over a target region, such as a surgical site, in a first tissue surface. The matrix material may be any continuous solid material, such as a sheet or film. After applying the material to the target region, the material is immobilized by applying energy over at least a portion of the surface of the matrix material which causes the material to fuse to the underlying tissue. The matrix material is preferably bioabsorbable so that it is resorbed by the body over time. Suitable matrix materials include proteins, polysaccharrides, and synthetic polymers.

22 Claims, 4 Drawing Sheets

U.S. PATENT DOCUMENTS

| | | |
|---|---|---|
| 5,134,229 | 7/1992 | Saferstein et al. . |
| 5,135,751 | 8/1992 | Henry et al. . |
| 5,156,613 | 10/1992 | Sawyer . |
| 5,156,839 | 10/1992 | Pennell et al. . |
| 5,194,473 | 3/1993 | Shinoda et al. . |
| 5,209,776 | 5/1993 | Bass et al. . |
| 5,264,540 | 11/1993 | Cooper et al. . |
| 5,266,326 | 11/1993 | Barry et al. . |
| 5,321,113 | 6/1994 | Cooper et al. . |
| 5,356,883 | 10/1994 | Kuo et al. . |
| 5,364,622 | 11/1994 | Franz et al. . |
| 5,366,735 | 11/1994 | Henry . |
| 5,380,536 | 1/1995 | Hubbell et al. . |
| 5,410,016 | 4/1995 | Hubbell et al. . |
| 5,422,376 | 6/1995 | Webb . |
| 5,503,638 | 4/1996 | Cooper et al. ............... 623/11 |

METHODS AND COMPOSITIONS FOR INHIBITING TISSUE ADHESION

This application is a continuation-in-part of application Ser. No. 08/673,710, filed Jun. 19, 1996 still pending.

BACKGROUND OF THE INVENTION

1. Field of the Invention

The present invention relates generally to surgical methods, and more particularly to methods for inhibiting tissue adhesion following surgical procedures.

Tissue adhesions occur frequently following surgery and may contribute to or cause compromised surgical results and post-surgical complications. Tissue adhesions may result from unwanted or excessive scar tissue and occur in various body regions including pelvic, abdominal, spinal, tendon, ophthalmic, urinary, thoracic and cardiovascular and are formed when normal tissue bonds to the surfaces of internal organs which have been traumatized or damaged during surgery. Such adhesions may join organs or other body tissues that normally are separate. Treating adhesions may necessitate additional surgery with additional costs, danger and/or discomfort to the patient.

Numerous procedures and materials have been proposed to minimize or eliminate post-surgical adhesions. Such procedures include introducing barrier materials such as metals, polymers, and natural materials over the target site. A woven material of regenerated cellulose is currently marketed for this purpose by Johnson & Johnson under the trademark Interceed®. This product, however, is not attached to tissue and remains unfixed in vivo. Other polymeric materials that have been tried for this purpose include nylon, cellophane, PTFE, polyethylene, siloxane, elastomers and polylactic acid copolymer films. Many of these materials are not biodegradable and therefore, remain in the body with unpredictable and potentially undesirable consequences.

For these reasons, it would be desirable to provide improved methods, compositions, and apparatus for inhibiting the formation of tissue adhesions following surgery and other trauma. It would be particularly desirable to provide anti-adhesion methods and compositions where a barrier layer can be formed and immobilized between tissues which are at risk of adhesion. The methods should be convenient to perform, be amenable to both open surgical and minimally invasive procedures, provide for firm anchoring of the anti-adhesion barrier at the target location of interest, and preferably utilize materials which are both biocompatible and resorbed by the body over time.

2. Description of the Background Art

WO 93/17669 describes particular hydrogel materials that may be applied to tissue, cross-linked by exposure to UV, and relied on for inhibiting tissue adhesion. U.S. patents relating to materials and methods for inhibiting tissue adhesion include U.S. Pat. Nos. 5,422,376; 5,410,016; 5,380,536; 5,366,735; 5,364,622; 5,365,883; 5,321,113; 5,266,326; 5,264,540; 5,194,473; 5,156,839; 5,135,751; 5,134,299; 5,126,141; 5,068,225; 5,017,229; 4,937,270; 4,937,254; 4,911,926; 4,889,722; 4,674,488; and 4,603,695. Published PCT applications relating to materials and methods for inhibiting tissue adhesion include WO 95/15747; WO 95/15343; WO 95/09883; WO 94/24962; WO 94/21324; WO 94/08635; WO 94/02517; WO 93/16687; WO 93/13137; WO 92/22312; and WO 92/21354. Published European applications relating to materials and methods for inhibiting tissue adhesion include 669 138; 645 150; 610 731; 608 921; 608 139; 426 368; 416 250; and 372 969. Other patents relating to applying energy to fusible materials to wound treatment include U.S. Pat. No. 5,071,417; U.S. Pat. Nos. 5,156,613; and 5,209,776. Copending related applications assigned to the assignee of the present application include U.S. Ser. Nos. 08/303,336; 08/461,227; 08/461,228 now U.S. Pat. No. 5,669,934; Ser. No. 08/481,712 now U.S. Pat. No. 5,690,675; and Ser. No. 60/011,898, the full disclosures of which are incorporated herein by reference.

SUMMARY OF THE INVENTION

The present invention provides improved methods, compositions, and apparatus for inhibiting the formation of adhesions between adjacent tissue surfaces. The risk of tissue adhesions typically arises following surgery on tissue surfaces which lie adjacent to other tissue surfaces, organs, or other body structures, where the natural healing process can cause unwanted tissue ingrowth between the healing tissue surface and the adjacent tissue surface. The situation can be exacerbated if two or more closely adjacent tissue surfaces are subjected to surgery or other trauma simultaneously.

According to the methods of the present invention, the formation of such tissue adhesions is inhibited by exposing a target region on at least one of the tissue surfaces and positioning a preformed layer of a matrix material over such target region. Energy is then applied to the matrix material in an amount sufficient to immobilize the matrix material over the target region. The adjacent tissue surfaces then reassume their natural juxtaposition, and the immobilized layer of matrix material inhibits adhesions therebetween.

The matrix material comprises a biologic substance or a biocompatible synthetic substance which will fuse or bond to underlying tissue upon application of energy from a suitable source, as described in more detail hereinafter. Preferably, although not essentially, the fusible material will be bioabsorbable so that it is resorbed over time, typically being resorbed within three months, preferably within one month, and often in 15 days or less. The matrix material need remain only until the tissue surfaces have healed sufficiently to resist adherence. Preferred is the use of biological materials, such as proteins and protein-containing mixtures, which are bioabsorbable and will bond to tissue proteins (e.g. covalently, non-covalently, physically, and combinations thereof) upon application of suitable activating energy. Exemplary proteins include collagen, gelatin, elastin, fibrinogen, fibrin, albumins, keratins, laminins, hemoglobins, and composites and mixtures thereof. Other biological materials include polysaccharides, such as glycosaminoglycans, starch derivatives, cellulose derivatives, agarose, alginate, and the like. In addition to biological materials, non-biological polymers may also find use, such as acrylates, polyvinyl resins, polylactate-glycolides, polycaprolactones, polyoxyethylenes, and the like. Each of these materials may be utilized alone, but will more frequently be employed together with a carrier substance, plasticizer, cross-linking agent, or the like. Exemplary matrix materials include collagen and gelatin combined with a plasticizer, such as poly(alcohols), e.g. glycerol or a polyethyleneglycol.

The matrix material will be applied to the target region as a preformed solid phase. By "solid phase," it is meant that the fusible material is preformed as a sheet, layer, film, strip, patch, mesh, or the like and placed over the wound region. Usually, the solid phase will be relatively dry, typically having a moisture content below 25% by weight, more usually below 15% by weight. Such dry materials are particularly convenient to store and manipulate, as described further below. The fusible material will be in the form of a solid or gel layer after energy has been applied according to the method of the present invention. That is, solid sheets, layers, films, strips, patches, and the like, may remain as a solid (although the dimensions may alter slightly as the material is softened and fused or tacked to the underlying tissue) or may be converted into gels as they absorb moisture from the tissue.

Optionally, the solid phase forms of the fusible material, such as sheets, layers, films, strips, and patches, may be reinforced with other fusible or non-fusible materials to reduce their fragility during the initial handling and placement. Usually, the reinforcement materials will also be bioabsorbable so that the reinforcement material will also be resorbed over time although perhaps at a different rate.

The methods of the present invention can rely on the application of energy from a wide variety of sources, including electromagnetic energy, particularly electrical energy, e.g. radiofrequency (RF) energy and microwave energy, infrared (heat) energy, and ultraviolet energy; optical energy, e.g. laser; mechanical energy, e.g. ultrasonic; and the like. Preferred is the use of RF energy which can be provided by conventional electrosurgical power supplies operating at frequencies typically in the range of 200 kHz to 1.2 MHz. Particularly preferred is the use of RF energy applicators which provide a uniform, dispersed energy flux over a defined area, such as inert gas beam RF energy sources, more particularly argon beam RF energy sources. Standard electrocautery devices could also find use.

The energy is applied in a pattern and manner suitable to immobilize the matrix material over the target region so that the material remains in place while the tissue surface heals. In the case of preformed films, sheets, and the like, it is necessary only to selectively apply energy to local areas (e.g. spots, lines, etc.) on the matrix material surface in order to "tack" the material to the underlying tissue. That is, in the region where energy has been applied, the matrix material will bond or otherwise fuse to the underlying tissue. In other regions, however, the matrix material will not be bound directly to the tissue, but will remain immobilized as a result of those areas where the film or sheet of material is bound. For example, the energy may be applied at least about the periphery of the preformed film or sheet in order to attach the edges of the sheet to tissue. Additional locations within the periphery may also be tacked by applying spots or other small areas of energy to the material. It will also be possible to apply the energy uniformly to a film or sheet of matrix material, thus resulting in substantially uniform bonding of the material to underlying tissue. Generally, however, it is preferred to only selectively bond or tack the material to the tissue. Surprisingly, it has been found that adhesion inhibition is superior when the solid matrix material has been "tacked" about the periphery and/or at spaced-apart interior locations than when it is fused uniformly over the entire surface.

DESCRIPTION OF THE SPECIFIC EMBODIMENTS

Figure 1:
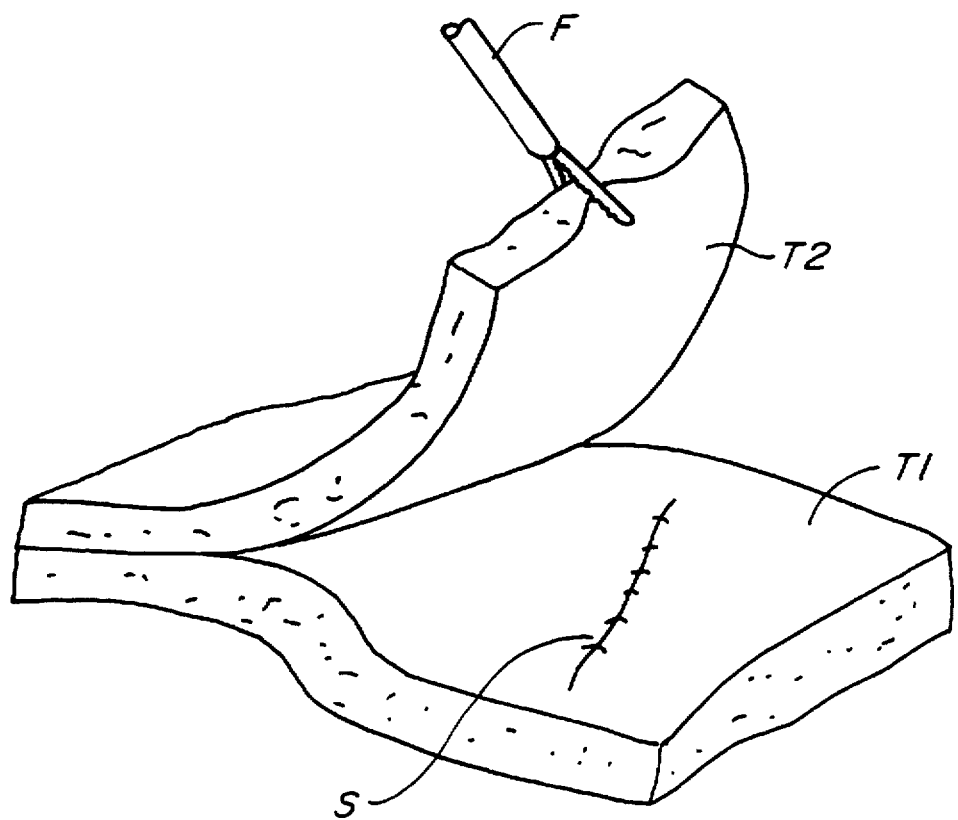
FIG. 1 is a schematic illustration of a pair of opposed tissue surfaces where one of the surfaces has a surgical lesion at risk of tissue adhesion.

Methods, compositions, and devices according to the present invention may be used for inhibiting the formation of tissue adhesions on or to any tissue subject to or at risk of adhering to an adjacent tissue surface. The present invention is particularly useful for inhibiting such tissue adhesions on tissue structures and organs, such as muscle, skin, epithelial tissue, connective or supporting tissue, nerve tissue ophthalmic and other sense organ tissue, vascular and cardiac tissues, gastrointestinal organs and tissue, pleura and other pulmonary tissue, kidney, endocrine glands, male and female reproductive organs, adipose tissue, liver, pancreas, lymph, cartilage, bone, oral tissue, mucosal tissue and the like. The methods will be particularly useful for treating surgical sites in a target region, where the surgical site may have been sutured, stapled, or otherwise closed prior to permitting the tissue surface to engage an adjacent tissue surface. The present invention provides for barriers formed from matrix materials, usually biodegradable matrix materials, between such tissue surfaces to inhibit or prevent the occurrence of tissue adhesions. As used hereinafter and in the claims, the terms "inhibit", "inhibiting", and "inhibition" will denote both total inhibition (i.e. prevention) and partial inhibition of adhesion.

The matrix materials may be any natural, modified natural, or synthetic substance which has the ability to be applied over the target region in a solid or non-solid state, and thereafter to be fused to the underlying tissue upon the application of energy from a suitable energy source. Thus, the fusible material will be able to create and/or maintain a solid, continuous film over (and sometimes penetrating into) the target region to form a barrier which inhibits or prevents the formation of adhesions between the target region and a corresponding region in an opposed tissue surface. Such fusible matrix materials should also be biocompatible (e.g., should be non-immunogenic and non-inflammatory), and usually (but not necessarily) will be bioabsorbable overtime (e.g., being partially or completely resorbed into the underlying tissue over a period from 3 days to six months).

Generally, the use of natural biological polymers, and in particular biological proteins, as the matrix material is preferred. Suitable proteins include collagen, gelatin fibrin, fibrinogen, elastin, albumins (including human serum albumin (HSA), bovine serum albumin (BSA), and ovalbumin), hemoglobins, combinations thereof, and the like, and mixtures and derivatives thereof. Particularly preferred is the use of collagen and modified collagens, such as gelatin (which is a protein-containing material obtained by hydrolysis of collagen in a well known manner), as described in application Ser. No. 08/303,336, filed on Sep. 9, 1994, the full disclosure of which is incorporated herein by reference. The fusible material will usually be applied to the target region as a solid layer, e.g., in the form of a film, sheet, patch, strip, mesh, or the like. Use of a mesh allows tissue to form a coagulum within the interstices of the mesh as energy is applied, as described in application Ser. No. 08/303,336, the disclosure of which is incorporated herein by reference.

The matrix material may alternatively comprise a polysaccharide component including one, two, or more individual polysaccharides. Exemplary polysaccharides include glycosaminoglycans such as hyaluronic acid, chondroitin sulfate, chitin, and chitosan; starch derivatives such as starch/hydroxyethyl starch; cellulose derivatives such as hydroxyethyl-cellulose, hydroxy propyl-methyl-cellulose, and carboxy-methyl-cellulose; agarose, and alginate.

In addition to the biological polymers described above, the matrix material may comprise one or more non-biologic polymers, usually in the form of a polymeric synthetic resin having a molecular weight above 10 kD, usually in the range from 25 kD to 500 kD. Exemplary non-biologic polymers include acrylates and acrylic resins such as polyacrylic acid, polyhydroxyethyl-methacrylates, and polyacrylamides; polyvinyl resins, such as polyvinyl alcohol (PVA) and polyvinylpyrrolidone; poly-organic acids and lactanes such as polylactate-glycolides and polycaprolactones; polyethylene oxides; and polypropylene oxides.

The polysaccharide, and non-biologic polymer, and combinations thereof, may comprise substantially all of the matrix material, or may comprise only a portion thereof. In the latter case, additional component(s) may be included, such as carrier substances, reinforcing materials, (e.g., reinforcing meshes, fibers, filaments, braids, and the like), and plasticizers, as described below.

The fusible matrix material will be a preformed solid, e.g., a film, sheet, patch, strip, mesh, or the like, and may optionally be reinforced with filaments, braids, meshes, and other woven and non-woven reinforcement materials. Preferably, the reinforcement materials will be bioabsorbable so that they will be resorbed together with the fusible matrix material. The solid phase forms of the fusible material may be formed by a variety of methods as described in copending application Ser. No. 08/303,336, the full disclosure of which has previously been incorporated herein by reference. Reinforcement materials can be added by various known techniques, such as impregnation, dipping, casting, co-extrusion, and the like.

In the preferred solid layer form, the fusible matrix material will initially be a relatively thin layer which can be cut or trimmed into a desired shape prior to application to the target region. The material layers will typically have a thickness in the range from 0.01 mm to 2 mm preferably from 0.04 mm to 0.5 mm. After application of the fusion energy, the fusible matrix material will be in the form of a continuous solid film or gel over the target region. That is, the layer of material may remain as a solid film, although the film will become bound to the underlying tissue and may alter in shape to some degree. Alternatively, the initial dry solid phase may be converted into a gel or gelatinous phase upon the application of energy and absorption of moisture from the underlying tissue. In the case of a fusible matrix material which is applied in the form of a mesh, the application of energy will usually form a coagulum of tissue within the interstices of the mesh, resulting in a solid or gelatinous, continuous film comprising both the fusible matrix material and the tissue coagulum after the energy has been applied.

In addition to the substances described above, the fusible matrix material of the present invention may further include dyes, pigments, and the like, which affect the energy absorption of the material in some desired manner. For example, particular dyes may be added to enhance absorption of energy from the selected energy source e.g., laser light or other optical energy. Additionally, dyes and pigments may be added simply to improve visualization of the material during use and/or permit materials having different characteristics to be distinguished from each other. Other substances and additives may be included with the fusible material for other purposes, as generally described in Parent application Ser. No. 08/303,336, filed on Sep. 9, 1994, the full disclosure of which has previously been incorporated herein by reference.

Protein and synthetic polymer matrix materials may further include glycosaminoglycans, such as hyaluronic acid, dermatan sulfate, chondroitin sulfate, and heparin. Use of the glycosaminoglycans may be desirable since such materials, which are anti-thrombotics, can further reduce adhesion to adjacent tissues and organs after the final solid or gelatinous layer has been formed by the application of energy.

The solid forms of the matrix material will preferably include a plasticizer to impart flexibility and toughness to the resulting film, sheet, or other structure. A suitable plasticizer will be biocompatible and preferably be resorbable so that they are resorbed together with the protein, polysaccharide, or synthetic polymeric component of the matrix material. Exemplary plasticizers include poly (alcohols), particularly polyalkylene alcohols and glycols, such as polyethylene glycol; polypropyleneglycol, sorbitol, and glycerol; and the like. Particularly preferred is polyethyleneglycol (PEG) having a molecular weight in the range from 200 to 3500, more preferably from 200 to 600. The placticizer, such as PEG, may be added to an aqueous solution or suspension of the protein or other matrix material to at least about 5–10%. The plasticizer may be added in the presence or absence of a crosslinker or both. The composition may also contain a viscosity enhancer such as a biocompatible polymer or sugar, such as maltose, mannitol, or PEG.

The solid forms of the fusible matrix material will typically be provided as sheets, strips, films, or patches having a thickness sufficient to provide mechanical integrity both before and after application to the target region. For most of the materials described above, and in particular for the collagen and gelatin materials, a thickness in the range from about 0.01 mm to 2 mm, with a preferred thickness from 0.04 mm to 0.5 mm is suitable. Most preferably, the thickness for the collagen and gelatin materials will be in the range from 0.04 mm to 0.1 mm. Fusible materials having thicknesses generally greater than the broad range are less suitable since they have poor energy absorption characteristics and display increasing stiffness. The peripheral dimensions of the continuous, solid sheets of fusible material are not critical. The sheets will typically be cut or trimmed to have a desired peripheral shape prior to use in the methods in the present invention.

The method of the present invention will utilize energy of a type and in an amount sufficient to fuse the fusible matrix material to underlying tissue. Suitable energy sources include electromagnetic energy, particularly electrical energy, e.g. radiofrequency (RF) energy and microwave energy, infrared (heat) energy, and ultraviolet energy; optical energy, e.g. laser; mechanical energy, e.g. ultrasonic; and the like. Preferred are the use of RF energy sources, such as those available as electrosurgical power supplies from companies such as Valleylab, Boulder, Colo., and Birtcher Medical Systems, Irvine, Calif., employing conventional RF-applying probes. Particularly preferred are radio frequency energy sources which provide for a dispersed or distributed current flow from a hand-held probe to the tissue. One such radio frequency energy source referred to as an inert gas beam coagulator which relies on flow of an inert ionizable gas, such as argon, for conducting current from the probe to the tissue.

Energy from the energy source will typically be manually directed to the fusible material overlying the tissue using a probe connected to an external power supply. The treating physician will manually direct the probe to apply energy over the surface of the fusible material and will visually confirm that fusion has been achieved. The probe may use conventional electrosurgical power supplies having an energy output from 2 W to 100 W, preferably from 20 W to 60 W. The fusible material will typically be exposed to the energy for a total time from about 5 seconds to 120 seconds, usually from 10 seconds to 40 seconds, for material having an area from 1 cm$^2$ to 10 cm$^2$. The precise timing will depend on the physician's visual assessment that fusion of the material to the underlying tissue has been achieved.

Referring now to FIGS. 1–5, exemplary methods according to the present invention will be described. Target regions which may be treated according to the method of the present invention will typically comprise a surgical interventional site S, such as a region which has been sutured, stapled, or otherwise surgically corrected, present in a first tissue surface T1 (FIG. 1). The tissue surface T1 may be in any of the tissues or organs set forth above, and will be opposed by a second tissue surface T2 which is retracted by conventional means, e.g., using surgical forceps F to expose the target region surrounding the interventional site S. It will be appreciated that the anti-adhesion procedures of the present invention will typically be performed immediately following the surgical intervention which results in the site S. The surgical procedures may be performed as part of conventional open surgical procedures, i.e., where an incision is made in the patient which is sufficiently large to permit direct line-of-site visualization and manipulation of instruments therethrough. The methods of the present invention will also be useful for performing minimally invasive surgical procedures, such as laparoscopic, thoracoscopic, endoscopic, arthroscopic, and similar procedures which are performed through percutaneous penetrations and while the target region is visualized under a viewing scope. The viewing scope will usually be a fiberoptic lens connected to a video display in a conventional manner, but can also be a surgical microscope, a magnifying glass, or a simple open cannula that provides direct visual observation of the target site. In the latter case, the matrix materials and energy-applying devices will be introduced through the percutaneous penetrations and manipulated under visualization through the viewing scope.

Figure 2:
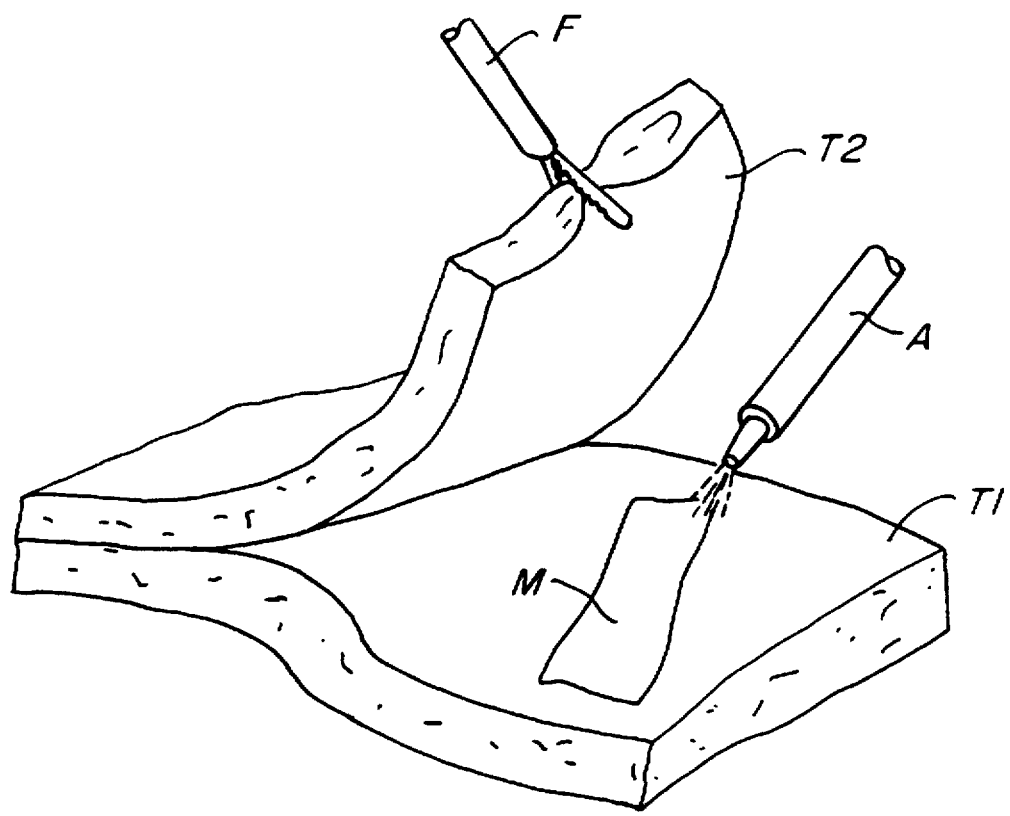
FIG. 2 illustrates a first protocol according to the method of the present invention for inhibiting tissue adhesion on the surgical lesion of FIG. 1.

After the surgical site S is exposed, as illustrated in FIG. 1, the matrix material will be applied at a location so that it will eventually be positioned between the surgical site S and tissue on the adjacent tissue surface T2. Usually, the material will be applied directly over the surgical site S, as illustrated in FIG. 2. In FIG. 2, a preformed film of matrix material M is placed over the surgical site S and energy is applied to immobilize the matrix material thereon. The energy applicator A may be any suitable device for providing any of the energy sources described above, usually being a laser, radiofrequency energy source, or the like. Preferred is the use of an inert gas beam coagulator, as illustrated in FIG. 2.

The energy may be applied to the matrix material M either in a continuous pattern so that the entire surface of the matrix material is exposed to energy, resulting in generally uniform bonding of the matrix material to the underlying tissue surface. Alternatively, the energy may be limited to smaller regions of the matrix material, such as about the periphery of the matrix material or at limited locations, i.e., spots within the matrix material so that the layer of matrix material is "tacked" in place. When using preformed film or sheets of matrix material, it is not necessary that the entire film or sheet be adhered to the underlying tissue. It is only necessary that sufficient bonding be achieved to assure that the material is immobilized and remains in place after the adjacent tissue surfaces T1 and T2 are allowed to resume their natural juxtaposition.

Figure 3:
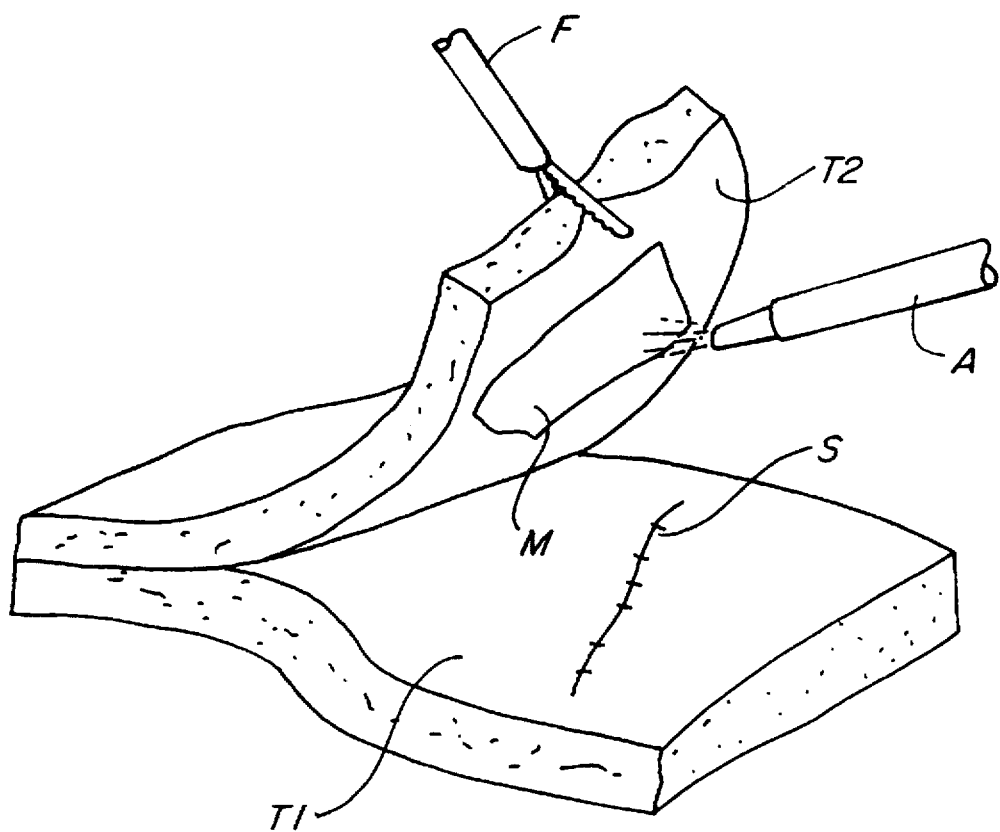
FIG. 3 illustrates a second protocol according to the method of the present invention for inhibiting tissue adhesion on the surgical lesion of FIG. 1.

It is not necessary that the matrix material M be placed directly over the surgical site S. As illustrated in FIG. 3, the matrix material M can be placed on the adjacent tissue surface T2 and fused thereto using the energy applicator A. By properly locating the matrix material M, the matrix material will be properly placed to provide the desired anti-adhesion barrier when the tissue surfaces T1 and T2 are permitted to resume their natural orientation.

Figure 4:
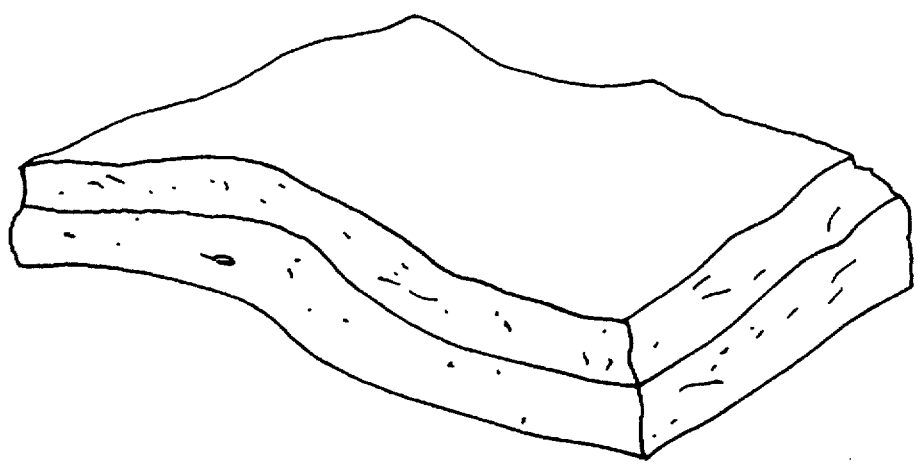
FIG. 4 illustrates the tissue surfaces of FIG. 1 after they have been treated by any of the protocols and released to reassume their natural juxtaposition.

In all cases, the matrix material which is in place after the tissue is allowed to come back into contact, as illustrated in FIG. 4, will remain in place for a time sufficient to inhibit adhesion of the tissue surface T2 with the surgical site S which is undergoing natural healing processes. Typically, the barrier will remain in place for at least about 3 days to a week, and often for much longer periods. It is generally desirable, however, that the matrix material eventually be resorbed so that the opportunity for immunogenic and other reactions is reduced.

The following examples are offered by way of illustration, not by way of limitation.

EXPERIMENTAL

Example 1

Materials and Methods for Collagen Patch Production and Methods for UV Crosslinking Collagen film materials were produced according to the following methods.

Formulations A, B & C: 26 grams of gelatin (280 bloom, Hormel Foods, Austin, Minn.) and 14 grams of PEG 400 MW (Union Carbide, Danbury, Conn.) were added with 1 L water for irrigation (WFI; deionized, depyrolyzed, and γ-ray sterilized) to a 2 liter reaction vessel. The solution was stirred and heated to 50° C. for 30 minutes. The solution was then cooled to 35° C., and aliquots of 13 mL were cast into 100×15 mm sterile square polystyrene petri dishes. The solution was evaporated at approximately 20° C. and 50% relative humidity (RH) to form films. Films were split into three groups: the first was cross-linked with 9999 mJ/cm$^2$ (Formulation A), the second with 5000 mJ/cm$^2$ (Formulation B), and the third with 18000 mJ/cm$^2$ (Formulation C). Cross-linking was performed with a SPECTROLINKER XL1500 UV (Spectronics Corp., Westbury, N.Y.) crosslinker equipped with 254 nm low pressure mercury bulbs.

Formulation D: 57.6 grams of gelatin as above and 14.4 grams of PEG 400 MW were added with 1.8 liter WFI to a 2 liter reaction vessel. The solution was stirred and heated to 50° C. for 20 minutes. The solution was then cooled to 35° C., and aliquots of 13 mL were cast into 100×15 mm sterile square polystyrene petri dishes. The solution was evaporated at approximately 20° C. and 50% RH to form films. The films were cross-linked with 9999 mJ/cm$^2$ in a SPECTROLINKER XL1500 UV crosslinker equipped with 254 nm low pressure mercury bulbs.

Formulation E: 40 grams of gelatin as above were added with 1 liter WFI to a 2 liter reaction vessel. The solution was stirred and heated to 50° C. for 30 minutes. The solution was then cooled to 35° C., and aliquots of 13 mL were cast into 100×15 mm sterile square polystyrene petri dishes. The solution was evaporated at approximately 20° C. and 50% RH to form films. The films were cross-linked with 3000 mJ/cm$^2$ in a SPECTROLINKER XL1500 UV crosslinker equipped with 254 nm low pressure mercury bulbs.

Formulation F: 451 g grams of collagen (Kensey Nash (Type F) Exton, Pa.) and 90 g of PEG 400 MW were added with 4500 mL WFI in a 5 liter reaction vessel. The solution was stirred and heated to 70° C. for 50 minutes. The material was then homogenized for 50 min. at 20,000 RPM in a Virtis Cyclone IQ$^2$ (Gardner, N.Y.) fitted with a 20 mm diameter rotor-stator and a flow-through head containing slotted orifices with a 1 mm gap. The solution was filtered through a 100 micrometer polypropylene mesh and water was added to adjust the solids content to 3.8% (w/w). The solution was cooled to 35° C., and aliquots of 13 mL were cast into 100×15 mm sterile square polystyrene petri dishes. The gelled solution was dried at approximately 20° C. and 50% RH to form films with water content of 11–15% w/w. The films were cross-linked with 3500 mJ/cm$^2$ in a SPECTROLINKER XL1500 UV crosslinker equipped with 254 nm low pressure mercury bulbs Formulation G: 156.0 grams of collagen (Kensey Nash (type F) Exton, Pa.) was added to 18.1 g of PEG 400 MW and 1500 mL WFI in a 5 liter reaction vessel. The solution was stirred and heated to 70° C. for 50 minutes. The solution was then filtered through a 100 micrometer polypropylene mesh. After filtering, the solution was adjusted to 3.8% solids w/w and then cooled to 35° C. Aliquots of 13 mL were cast into 100×15 mm sterile square polystyrene petri dishes. The solution was dried at approximately 20° C. and 50% RH to form films. The films were cross-linked with 3500 mJ/cm$^2$ in a SPECTROLINKER XL1500 UV crosslinker equipped with 254 nm low pressure mercury bulbs.

The formulations are summarized in Table 1 below.

TABLE 1

| Formulation | Gelatin | Platicizer % by weight | UV Xlinked in mJ/cm$^2$ |
| --- | --- | --- | --- |
| None/Control | Surgery only | N/A | N/A |
| A | Hormel gelatin 65% | PEG 400 35% | 5000 |
| B | Hormel gelatin 65% | PEG 400 35% | 9999 |
| C | Hormel gelatin 65% | PEG 400 35% | 18000 |
| D | Hormel gelatin 80% | PEG 400 | 9999 |
| E | Hormel gelatin 100% | none | 3000 |
| F | Kensey Nash collagen 83% | PEG 400 17% | 3500 |
| G | Kensey Nash collagen 89.6% | PEG 400 10.4% | 3500 |

Example 2

Materials and Methods for Creating and Measuring Adhesions

The collagen and gelatin films prepared in Example 1 (A and D–G) were tested for their ability to prevent abdominal adhesions in a rat cecum—body wall adhesion model.

Creation of Wounds

Sprague Dawley rats (84) having weights of 240–280 grams at the time of surgery were used. This animal model is recognized as a standardized model in which a single, specific adhesion can be objectively measured (Harris (1995) Surgery; 117:663–9). The testing procedure was as follows:

The animals were anesthetized with an intramuscular injection of ketamine hydrochloride in combination with xylazine. The abdomen of each animal was clipped with electric clippers, and the skin was scrubbed with iodophor and rinsed with 70% alcohol. A 6 cm midline skin incision was made at the abdomen, and the skin retracted. A 4 cm incision was made through the abdominal wall. The abdominal wall was also retracted. A defect in the abdominal wall of each animal was created approximately 1 cm lateral to the midline incision. This defect was created by excising a 1×2 cm segment of parietal peritoneum, including a superficial layer of muscle. The cecum was then elevated and positioned so that at closure, the cecum will contact the abdominal wall defect. A 1×2 cm defect was then created on the serosal surface of the cecum. The cecum was abraded by scraping with a scalpel blade so that a homogenous surface of petechial hemorrhage was created over the abraded area. The abdominal wall defect was abraded in a similar manner. Both abraded areas (the cecum and body wall) were exposed to air for 10 minutes.

Control Animals

After exposure to air, the cecum defect and abdominal wall defect were placed in contact, and the midline incision closed with a 4-0 absorbable suture. The skin was closed with 4-0 silk suture or surgical staples.

Use of Different Patch Materials

Under sterile conditions, patch materials A and D–G were cut into 3×5 cm pieces. After air drying for ten minutes, a surgical defect (either abdominal wall or cecum) in each animal was covered with one of the previously prepared test patches. The patch was subsequently attached either at the periphery (tacked at the corners) or uniformly over the entire area of the patch by applying energy with an argon beam coagulator ABC 6400®, CONMED, Ithaca, N.Y. The patch-covered defect was placed into contact with the opposing tissue plane, the midline incision was closed with a 4-0 absorbable, and the skin was closed with 4-0 silk suture or surgical staples.

Seven days following surgery, all control and test animals were euthanized in a manner consistent with the Recommendations of the AVMA Panel on Euthanasia. Subsequently, the strength of adhesions were measured and compared between the various formulations. The results are summarized below in Table 2.

TABLE 2

| Formulation | Location of Patch | Method of attachment | No. of Animals | % animals with adhesions |
| --- | --- | --- | --- | --- |
| None/Control | | | 5 | 80 |
| A | Body Wall | Tacked | 5 | 0 |
| D | Body Wall | Tacked | 5 | 40 |
| E | Body Wall | Tacked | 5 | 40 |
| F | Body Wall | Uniform | 10 | 40 |
| | Body Wall | Tacked | 14 | 7 |
| | Cecum | Tacked | 10 | 10 |
| G | Body Wall | Tacked | 10 | 30 |
| | Body Wall | Uniform | 10 | 30 |
| | Cecum | Tacked | 10 | 10 |

Example 3

Materials and Methods for Various Test Methods

Nine physical characteristics of the test film formulations were measured as follows.

Thickness

A Mitutoyo Thickness Gauge Model, IDC Mitutoyo Corp., Japan was used to determine the thickness of collagen/gelatin films. Using the release cable or the lifting lever, the thicknesses at each corner and at the center of the film were measured, for a total of 5 measurements on each film.

Percent Swell

The amount of saline absorbed by collagen/gelatin during a 22±1 hour incubation was determined as follows. Saline solution (0.9% w/w 5 mL) was added to each scintillation vial containing a test sample. The films were hydrated for 22±1 hours at 20°–25° C. The percent swell was calculated as follows:

$$\frac{(\text{Hydrated Weight of Film}) - (\text{Dry Weight of Film})}{\text{Dry Weight of Film}} \times 100\%$$

Denaturation Temperature

The denaturation temperature of the collagen/gelatin components of the test films and collagen raw material were determined using a DSC 2910 Differential Scanning Calorimeter (DSC), TA Instruments, New Castle, Del. 1.0–3.0 mg of patch sample plus 0.9% w/w sodium chloride solution (13±0.4 µl) were added to an aluminum pan and hermetically sealed. Heating rates were 5° C./min or 10° C. min. Peak temperatures and enthalpy of melting were recorded.

Pliability

The pliability of each collagen/gelatin film was determined as follows. The force required to bend the collagen/gelatin film through a defined distance was measured, and the bending modulus calculated from the equation given in the Machinery's Industrial Press, Inc., NY, 21$^{st}$ Edition, 1980. A film sample was placed in the clamp on a Swiss Height Gauge so that 8 mm of patch was free. The force required to bend the patch through a deflection of 2 mm was measured.

Tear Test

Figure 5:
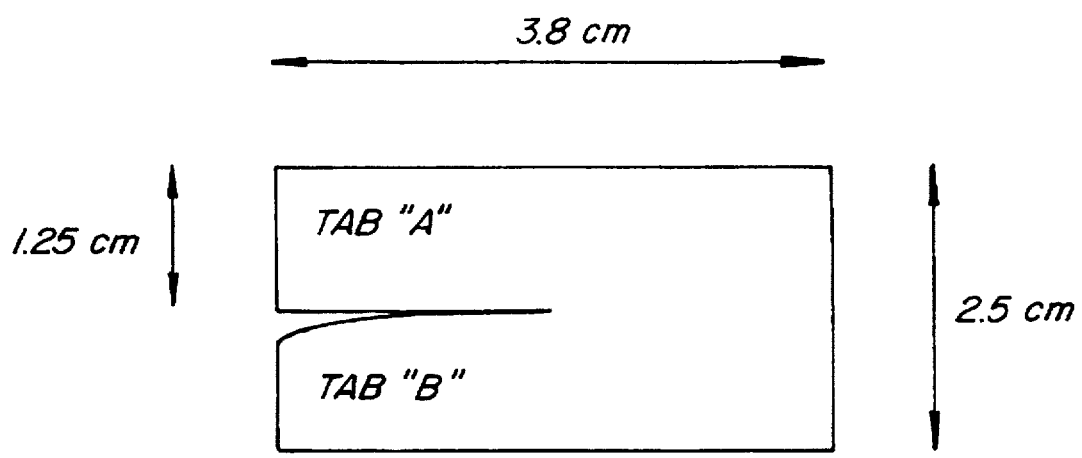
FIG. 5 illustrates the dimensions of test films used to measure tear force in the Experimental section below.

The force required to propagate a tear in collagen/gelatin films was calculated using a 3.8×2.5 cm rectangular piece from the test film having the shape and dimensions shown in FIG. 5. The force to tear between tabs A and B was measured using a Chatillon tester (TDC 200 test stand fitted with 250 g or 2.25N load cell, DGGS 250 g digital force gauge).

Tensile Strength and Strain at Failure

Tests were performed with a Chatillon TCD 200 fitted with a digital force gauge (Chatillon Instruments, Greensboro, N.C.), connected to an XY plotter. Film samples were typically 1×3 cm and were glued to polystyrene tabs with cyanoacrylate (Superglue). Films and tabs were hydrated for precisely 1 min. in 0.9% (w/w) sodium chloride and blotted briefly. The plastic tabs were clamped in the jaws of the tester, which assured that tensile failure occurred within the sample and not at the point of clamping. Stress was computed as force in Newtons divided by the original cross-sectional area (determined from thickness and width of test films); percent strain at failure was $\Delta l/l_0 \times 100$ where $\Delta l$ is the change in length and $l_0$ is the original sample length.

Elasticity (%)=(amount of sample stretch×100)/10

Loss on Drying

Weight loss on drying of collagen/gelatin films, raw material collagen, slurries, and solutions were determined by placing the test samples into an oven which had been set at 120°±5° C. The sample remained in the oven for at least 20 minutes after the oven had reached its set temperature. Percent loss on drying was calculated using the following formula:

$$\text{Percent loss on drying} = \frac{(\text{wet sample weight} - \text{dry sample}) \times 100}{\text{wet sample weight}}$$

Percent solids was calculated using the following formula:

$$\text{Percent solids} = \frac{\text{dry sample weight} \times 100}{\text{wet sample weight}}$$

Collagenase Digestion

Film samples were cut into disks 6 mm in diameter, using a steel punch. Such disks typically weighed 2–3 mg and were between 0.04 and 0.07 mm thick. The sample disks were placed in 2.0 ml of a digestion buffer (Tris-HCl, pH 7.5, 0.05M, containing 0.005M $CaCl_2$) plus 120 µl of a Clostridial collagenase solution. The collagenase was prepared at 300 units/ml in 0.05M Tris-HCl, pH 7.5, containing 0.0005M $CaCl_2$. Enzyme units were as given by the manufacturer, based on hydolysis of furylacryloyl-Leu-Gly-Pro-Ala. The level of enzyme was sufficient to be in excess for all film samples taken. The sample in buffer and enzyme was incubated with shaking at 37° C. until the sample disk disintegrated, which was scored as digestion time.

The results of these tests for formulations B–G are summarized in Table 3 below.

TABLE 3

| | Formulation: | | | | | |
|---|---|---|---|---|---|---|
| Test Method | B | C | D | E | F | G |
| Thickness (mm) | 0.054 | 0.053 | 0.054 | 0.053 | 0.046 | 0.049 |
| % Swell | 402 | 293 | 293 | 285 | 321 | 510 |
| DSC Peak (°C.) | 33.7 | 35.5 | 35.5 | 36.7 | 35.5 | 35.2 |
| Pliability (mN) | 1.4 | 1.4 | 1.4 | 1.5 | 1.5 | 3.2 |
| Tear test (N) | 0.022 | 0.025 | 0.025 | 0.040 | 0.018 | 0.019 |
| Tensile strength at failure (N/cm$^2$) | 106 | 313 | 307 | 136 | 174 | 361 |
| Strain at Failure (%) | 55 | 54 | 54 | 58 | 44 | 97 |
| Loss on drying (%) | 12.2 | 13.3 | 13.3 | 21.7 | 11.9 | 15.5 |
| Collagenase Digestion (min.) | 10 | 60 | 60 | 33 | 42 | 18 |

Although the foregoing invention has been described in some detail by way of illustration and example, for purposes of clarity of understanding, it will be obvious that certain changes and modifications may be practiced within the scope of the appended claims.

What is claimed is:

1. A method for inhibiting the formation of adhesions between adjacent tissue surfaces, said method comprising:

exposing a target region on at least one of the tissue surfaces;

positioning a preformed, biocompatible, resorbable solid layer of matrix material having a thickness of about 0.01 mm to 2 mm over the target region;

applying about 2 W to 100 W energy to the matrix material over a region for approximately 5 seconds to 120 seconds and in an amount sufficient to immobilize the matrix material layer over the target region; and permitting the adjacent tissue surface to reassume their natural juxtaposition, wherein the immobilized layer of matrix material inhibits adhesions therebetween.

2. A method as in claim 1, wherein the target region is a surgical site and at least one of the tissue surfaces is retracted to expose the target region.

3. A method as in claim 2, wherein the surgical site is in tissue selected from the group consisting of muscle, skin, epithelial tissue, connective or supporting tissue, nerve tissue, ophthalmic and other sense organ tissue, vascular and cardiac tissues, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue.

4. A method as in claim 2, wherein the surgical site is open to permit both positioning of the layer of matrix material and applying energy to the matrix material.

5. A method as in claim 1, wherein the target region is accessed by:
   forming at least two percutaneous penetrations in close proximity to the target site;
   introducing a viewing scope through one of said penetrations;
   viewing the surgical site using said viewing scope;
   positioning the matrix material through another of the penetrations while viewing; and
   applying energy through another of said penetrations while viewing.

6. A method as in claim 1, further comprising a step of shaping the matrix layer to conform to the dimensions of the target region prior to positioning the layer over said target region.

7. A method as in claim 1, wherein the matrix material comprises at least one of a biologic polymer and a synthetic organic polymer.

8. A method as in claim 7, wherein the matrix material comprises a protein selected from the group consisting of collagen, gelatin, fibrin, fibrinogen, elastin, albumins, keratins, laminins, hemoglobins, and combinations thereof.

9. A method as in claim 7, wherein the matrix material comprises a polysaccharide selected from the group consisting of glycosaminoglycans, starch derivatives, cellulose derivatives, agarose, and alginate.

10. A method as in claim 7, wherein the matrix material comprises a non-biologic polymer selected from the group consisting of acrylates, methacrylates polyvinyl resins, polylactate-glycolides, polycaprolactones, and polyoxyethylenes, wherein the non-biological component of the matrix material has a molecular weight below approximately 10 kD.

11. A method as in claim 7, wherein the matrix material may optionally contain a plasticizer.

12. A method as in claim 11, wherein the plasticizer is selected from the group consisting of polyethylene glycol, sorbitol, and glycerine.

13. A method as in claim 12, wherein the matrix material comprises from 70% to 95% by weight collagen and from 5% to 30% by weight PEG with a molecular weight in the range from 200 to 3500.

14. A method as in claim 13, wherein the matrix material further comprises a plasticizer.

15. A method as in claim 12, wherein the matrix material comprises from 70% to 95% by weight gelatin and from 5% to 30% by weight PEG with a molecular weight in the range from 200 to 3500.

16. A method as in claim 15, wherein the matrix material further comprises a plasticizer.

17. A method as in claim 1, wherein the applied energy is selected from the group consisting of radio frequency energy, microwave energy, infrared energy, ultraviolet energy laser energy, and ultrasonic energy.

18. A method as in claim 17, wherein the energy applying step comprises directing energy from a radio frequency inert gas coagulator applicator against the target region.

19. A method as in claim 1, wherein the matrix material comprises collagen or gelatin and the energy is applied at a level from 1 $W/cm^2$ to 100 $W/cm^2$ for a time sufficient for the material to fuse to the tissue.

20. A method as in claim 1, wherein the energy is applied to selected locations on the solid layer of matrix material only, whereby the material is fused to tissue underlying the target region.

21. A method as in claim 20, wherein the energy is applied at least about the periphery of the solid layer of matrix material.

22. A method as in claim 1, wherein the energy is applied over substantially the entire exposed surface of the matrix material, whereby the material is uniformly fused to tissue underlying the target region.

* * * * *